United States Patent [19]
Shikinami

[11] Patent Number: 5,711,960
[45] Date of Patent: Jan. 27, 1998

[54] BIOCOMPATIBLE IMPLANT MATERIAL COMPRISING A TRI-AXIAL OR MORE THREE-DIMENSIONAL FABRIC

[75] Inventor: Yasuo Shikinami, Osaka, Japan

[73] Assignee: Takiron Co., Ltd., Osaka, Japan

[21] Appl. No.: 449,560

[22] Filed: May 24, 1995

Related U.S. Application Data

[63] Continuation-in-part of PCT/JP94/01565, Sep. 22, 1994.

[30] Foreign Application Priority Data

Sep. 24, 1993 [JP] Japan ............................ 5-261582

[51] Int. Cl.$^6$ .................................. A61F 2/28; B32B 1/08
[52] U.S. Cl. .......................... 424/426; 424/425; 428/36.1; 428/36.3
[58] Field of Search ........................ 424/423, 425, 424/426; 428/36.1, 36.3

[56] References Cited

U.S. PATENT DOCUMENTS

| | | | |
|---|---|---|---|
| 3,987,797 | 10/1976 | Stephenson | 424/423 |
| 4,089,071 | 5/1978 | Kalnberz et al. | |

FOREIGN PATENT DOCUMENTS

| | | |
|---|---|---|
| 0338976 | 10/1989 | European Pat. Off. |
| 0366018 | 5/1990 | European Pat. Off. |
| 0511686 | 11/1992 | European Pat. Off. |
| 0560279 | 9/1993 | European Pat. Off. |
| 2635966 | 3/1990 | France |
| 3042003 | 7/1982 | Germany |
| 04129564 | 4/1992 | Japan |
| 2215209 | 9/1989 | United Kingdom |

OTHER PUBLICATIONS

"Design and In Vitro Testing of Newly Made Biocomponent Fabrics for Vascular Surgery", Chu et al, Polymer. Mater. Sci. Eng. (1985), 53, 400–4.

*Primary Examiner*—Carlos A. Azpuru
*Attorney, Agent, or Firm*—Sughrue, Mion, Zinn, Macpeak & Seas, PLLC

[57] ABSTRACT

This invention provides an implant material which has high mechanical strength and durability in three-dimensional directions and a function to synchronize with deformation characteristics of surrounding biological tissues, is capable of being penetrated by biological tissues into its fabric space, and does not cause foreign body reaction or can positively connect with biological tissues, so that it can be implanted in the living body for a prolonged period of time. It uses, as a base material, a biocompatible bulk structure of a three-dimensionally woven or knitted fabric of organic fibers or a composite fabric thereof, and its void ratio in the fabric is preferably set to 20 to 90 vol %. More preferably, the surface of organic fibers which constitute the bulk structure is biologically activated or inactivated.

16 Claims, 4 Drawing Sheets

STRAIN-STRESS CURVE

COMPRESSION STRESS-STRAIN CURVE

LOAD-STROKE CURVE

BIOCOMPATIBLE IMPLANT MATERIAL COMPRISING A TRI-AXIAL OR MORE THREE-DIMENSIONAL FABRIC

This is a continuation-in-part application of PCT/JP94/01565, filed Sep. 22, 1994.

TECHNICAL FIELD

This invention relates to an implant material which has biocompatibility.

BACKGROUND ART

Fibers have high strength in the direction of extension of the molecular chain due to the molecular orientation. Accordingly, from ancient times of human beings, they have been used as cloth by weaving them into a plane fabric. It, however, is basically development of fabrics in two-dimensional direction.

Three-dimensional fiber composite materials (3-DC: three-dimensional composites) which are materials in which a heat resistant and high strength material is filled as a matrix into fiber space created by three-dimensional weaving and knitting of yarn have been put into various examination since about 30 years ago during the process of space rocket development with the aim of developing a material which has high strength in three-dimensional direction and does not cause strain under high temperature. However, they are examined mainly as aircraft and industrial materials to be used under severe environment, and they have not applied to biomedical materials which are used for a long period of time under different severe environmental conditions, namely implant materials which are implanted in the living body. An exceptional case is an artificial blood vessel made of polyester fibers in a tubular form having thin wall thickness, which is triaxial fabric or triaxial weaving having three-dimensional expansion. However, this vessel is a fabric product in which threads of three axis direction are crossed at an angle of 60° in the same plane, which has been developed with the aim of improving anisotropy (bias) of plane fabric and, therefore, is a cylindrical fabric corresponding to a triaxial-two-dimensional reinforcing type. Another exceptional case is an artificial ligament in the shape of a cord made of polyester or polypropylene, which is woven as a monoaxial three-dimensional braid (3-DB: three-dimensional braid). However, a cubic body of a three-dimensional fiber architecture (3-DF: three-dimensional fabrics) having certain size and volume and clear cubic shape (design) and strength, namely a bulk structural body has not been applied to a biological material (biomaterial) as an implant.

In recent years, information about implants from the viewpoint of engineering, material science, medical science and physiology has at last been accumulated rapidly, resulting in the practical use of some artificial implants. However, conventional three-dimensional fiber composite materials (3-DC) for industrial and space aircraft engineering use cannot be applied directly to medical purpose because of their fatal problem in terms of physiological and mechanical biocompatibility.

That is, since materials of the conventional three-dimensional fiber composite materials (3-DC) for industrial and space engineering use are inorganic composite materials comprising a carbon and various ceramic fibers and matrixes thereof in a composite form, they cannot be used in the living body as biomaterials because of the lack of many basic requirements for the biocompatible material, such as functionality, biological safety, biocompatibility, sterilizability, and the like.

On the other hand, some implants made of other materials than fiber reinforced composite materials have already been put into trial or practical use. For example, since inorganic materials such as metals (stainless steel, titanium and its alloy, nickel, cobalt alloy and the like), composite materials (composites of carbon and thermosetting resins) and ceramics (alumina, zirconia, hydroxyapatite and the like) are possessed of advantages such as high strength, high toughness, abrasion resistance, corrosion resistance and the like, they have been put into trial and practical use as hard tissue filling/prosthetic or surgical auxiliary materials which require basically high strength, though the number of such cases is small. However, some problems still remain unsolved such as corrosion and fatigue in the case of metals, low toughness and excessively high rigidity in the case of ceramics and interface destruction in the case of composite materials of inorganic materials with organic polymer materials.

On the other hand, examples of organic polymer materials to be used by implanting in the living body include, though not so many, polymethylmethacrylate (PMMA), polydimethylsiloxane (silicone), polytetrafluoroethylene (PTFE), polethylene terephthalate (PET), polypropylene (PP), (ultra-high molecular weight) polyethylene (UHMWPE) and the like. Taking their advantages of physical properties such as flexibility, abrasion resistance, impact absorbability, durability and the like, these materials are mainly used as substitutes for softer tissues in comparison with inorganic materials. These synthetic polymers, however, do not have sufficient properties required for implant materials. That is, there are remaining problems of insufficient biocompatibility both from mechanical and physiological points of view, such as mismatching in mechanical characteristics with the living body region to be implanted, insufficient durability and strength and insufficient chemical surface characteristics and chemical and structural morphology of the material in view of their affinity for the living body. In any case, there still is an unstopping demand for the development of a material having more excellent biocompatibility.

The term "compatible with the living body" means that the material shows moderate interaction with the living body, is not recognized as an invasive foreign material and does not cause a so-called foreign body reaction. That is, it means that the material shows no recognition reaction as a foreign body both mechanically and physiologically. In other words, since biocompatibility is a positive property of well adapting to the living body, it is necessary to fully examine interaction between the material and the living body. The biocompatibility can be divided roughly into the interaction with the living body through the surface of the material and another interaction in which properties of the material as a bulk structure exerts influence on the surrounding living body tissues. These interactions are different from the safety (toxicity) to the living body caused by low molecular weight compounds such as remaining monomers, oligomers or the like eluted into the living body from the aforementioned organic polymer materials.

Materials having excellent biocompatibility can be divided into (1) those which have mutually inviolable relation between the material and the living body, namely those which are bioinert in the living body and (2) those which are bioactive in the living body and capable of binding to the surrounding tissues. That is, like the case of (1), certain implants capable of showing no foreign body reaction do not cause or require positive binding to the living tissues.

However, like the case of (2), it is necessary sometimes to effect binding to hard tissues such as bones or teeth or to soft tissues such as the skin. In any case, the biocompatibility of not causing strong stimulation to the living body is absolutely necessary, especially in the case of implants which contact with the living body for a prolonged period of time.

In summary, the biocompatibility can be divided roughly into (A) non-stimulative property (non-foreign body reactivity) and (B) tissue connectivity, and (A) can further be divided into (i) surface compatibility and (ii) bulk compatibility. The case of (i) is further divided into no complement activations, no thrombus formation, and no tissue damage in short-term and no encapsulation, no tissue hyperplasia, and no calsification in long-term. The case of (ii) is a long-term property and relates to mechanical and structural consistency such as of compliance, design and the like. The case of (B) relates to the growth quality of bone tissues and soft tissues or the non-growth quality of dentin. The classification of biocompatibility mentioned above is described in detail in Biocompatible Materials<Their Functions and Applications>edited by Yoshito Ikada (Nippon Kikaku Kyokai), and the definition of related terminology is described in D. F. Williams "Progress in Biomaterial Engineering, 4 Definitions in Biomaterials" (1987) (Elsevier).

When biological tissues are observed macroscopically as a bulk (cubic structure), there are a portion having a mechanically, chemically and morphologically planar or steric directionality (anisotropy) and a isotropic portion which does not have such a directionality. However, it can be said that a tissue which is uniform and homogeneous in all directions hardly exists. In any case, each tissue is possessed of respectively different characteristics in three-dimensional directions as a bulk. In consequence, when a biomaterial having mechanical and structural consistency is produced, it is necessary to prepare a material having mechanical and structural properties in three-dimensional directions which are similar to those of the biological tissue. At the same time, the material should satisfy chemical and physiological surface compatibility. In addition, it sometimes should have specific surface, structural morphology and shape so that it can positively provide an area causing strong binding with the living body.

However, most of the conventional artificial materials are produced taking only two-dimensional directions into consideration. In other words, they have no mechanical, chemical and morphological directionalities in each of the three-dimensional directions and, as a consequence, they are anisotropic materials, which are not intentionally required. For example, it is unavoidable that most of sintered materials of a single metal, ceramics and the like are ready isotropic and that organic polymer materials have anisotropic nature to some extent. Such facts are principal phenomena which cannot be avoided when a cubic structure is produced by a certain molding method. Though it is possible to intentionally produce an isotropic or anisotropic material by compounding organic and inorganic materials, it still is difficult to develop it into three-dimensional directions. The reason for this difficulty is that development and control in three-dimensional directions simultaneously with two-dimensional directions is nearly impossible and difficult from the viewpoint of production techniques. Thus, because it is difficult to produce even a cubic structure in which its characteristics in three-dimensional directions are intentionally controlled, there is no case which rendered possible application of a three-dimensional structure having intentionally controlled mechanical directionality to implants.

However, as has been described in the foregoing, it is essential for the production of a closely ideal implant material to develop a material which has surface compatibility, at the same time having mechanical and structural consistency in three-dimensional directions, and can provide a positive or spontaneous binding area so that the implant and the living body can bind strongly to each other, if required.

The present invention has been accomplished with the aim of solving these problems, and its essence resides in the use of a three-dimensional fiber architecture having biocompatibility as biomaterials in implants.

DISCLOSURE OF THE INVENTION

The aforementioned implant material whose surface and bulk do not act as a foreign body against the living body and which can provide a chance and area for its binding to the surrounding tissue can be provided by a biocompatible fabric structure in the form of a bulk comprising a three-dimensional woven or knitted fabric of organic fibers or a assorted fabric thereof. The term "bulk" as used herein means "a material which has certain size and volume and a clear cubic shape (contour)", and a fabric bulk structure means a structure which consists of a three-dimensional fiber architecture (3-DF) having such certain size, volume and cubic shape (contour). The cubic shape is not particularly limited, provided that it has certain size and volume. The implant material of the present invention comprises a three-dimensional fiber architecture (3-DF) as its basic constituting structure which can be obtained by the process described in detail in the following. The implant material comprising this three-dimensional fiber architecture may be produced in the following manner.

(1) Bioinert, bioaffinitive or bioactive yarn and roving are subjected to three-dimensional weaving and knitting to be used as a bioinert, biocompatible or bioactive 3-DF implant material.

(2) Roving and yarn are subjected to surface treatment to provide the surface with bioinertness, bioaffinity or bioactivity and then woven and knitted into 3-DF to be used as an implant material.

(3) After weaving and knitting 3-DF, an implant material is obtained by treating the structure in such a manner that its surface becomes entirely or partially bioinert, bioaffinitive or bioactive.

As a matter of course, it is possible to combine these processes. In each case, the three-dimensional woven and knitted fabric architecture may be used as it is or after coating it with the same or different material or after filling the same or different material as a matrix in the fabric space to construct a reinforced fabric structure.

Next, the fabrics of woven materials are generally classified based on the mode of construction.

Various types of fabrics can be classified using the corresponding dimensional number and the axial number, with expressing the geometric shape of the material by the dimensional numbers and expressing the azimuth number of fiber arrangement by the axial number. That is, a plane body arrangement system such as a prepreg sheet in which rovings are arranged in parallel in one direction is uniaxial-two dimensional. Arrangement of plain weaving, satin weaving and the like woven by using warp and weft is diaxial-two dimensional. Triaxial weaving obtained by improving anisotropy (bias) of a plane weaving is a weaving in which threads of triaxial directions are crossed at an angle of 60° in the same plane and, therefore, is triaxial-two dimensional. An arrangement in which warp, weft and vertical yarn are three-dimensionally developed is a triaxial-three dimensional weaving. Also, there is a multiaxial-three dimensional weaving in which fibers are arranged in multiaxial azimuth such as 4, 5, 6, 7, 9, and 11 axes, or the like.

Next, three-dimensional weaving is classified based on their axial numbers.

a. Uniaxial-three dimensional fabric

A cubic weaving obtained by changing the arrangement order of threads arranged in parallel in one direction, and braids and laminated structures belong to this type. They are produced by various types of braider and magna-weave. Since arranging order of threads can be changed relatively freely and a contour can be obtained easily in response to the shape of the product, this method is advantageous for producing structural materials having I form or circular sections and materials having complex shapes.

In this connection, braids produced by this method using polyethylene terephthalate or polypropylene have already been used in artificial ligament. However, the present invention does not use a braid as an implant of the final object, but aims at a three-dimensional fiber structure having more high processability making use of the three-dimensionalization techniques and utilizes the techniques for the uniaxial-three dimensional fabric as a means to obtain the intended structure.

b. Diaxial-three dimensional fabric

A multi fabric weaving composed of two components of yarns, i.e., warp and weft. An H form structure belongs to this type. It can be woven by conventional weaving machine. The thickness is limited to about 20 layers, and a weaving having a complex cubic structure cannot be manufactured.

c. Triaxial-three dimensional fabric

A weaving in which warp, weft and vertical yarn are three-dimensionally arranged. Its shape can be divided roughly into thick plate (block) and cylindrical forms. A honeycomb-type structure belongs to this type.

This triaxial-three dimensional fabric can be roughly divided as follows.

(i) Orthogonal fabric and angle interlock (non-orthogonal fabric)

Orthogonal fabric: a fabric in which a third yarn (penetrating yarn) is orthogonally arranged in such a way that it binds plane threads linearly arranged in longitudinal and transverse directions. FIG. 1 shows a concept of this fabric structure.

Non-orthogonal fabric: a fabric in which the warp yarn of (i) is arranged in non-orthogonal fashion by changing its working timing. FIG. 2 shows a concept of this fabric structure.

(ii) Leno fabric

A fabric in which threads of two directions in a plane are held between two vertical threads to fix intersection points.

Plates and blocks are obtained in (i) and (ii).

(iii) Cylindrical fabric

A fabric made of three directions of circumferential yarn, radial yarn and axial yarn, characterized by the cylindrical orientation of fibers.

d. n-Axial-three dimensional fabric

A three dimensional fiber architecture of multiaxial arrangement such as 4, 5, 6, 7, 9, or 11 axes and the like is possible in order to obtain a reinforced base material which is more isotropic than three directions. FIG. 3 and FIG. 4 respectively show concepts of 4 axes and 5 axes fabric structures.

The above examples are three-dimensional weavings of simple shapes such as plate, block, rod, cylinder and the like which are classified on the basis of the number of axes. In comparison with this, the following e. can be classified as a three-dimensional weaving having a complex shape, attaching importance to its contour.

e. Three dimensional complex form

A three-dimensional weaving having a complex shape close to the final shape is integrally formed. For example, an I-beam, a T-beam, a hat shape, a honeycomb shape, a tapered plate and the like can be formed at will. They are produced by plain weave, twilled weave, leno weave and the like.

Respective processes for the production of the above three-dimensional fabrics are described in detail in Frank K. Ko "Recent Advances in Textile Structure Composites" (1985), pages 83 to 94; Preform Fiber Architecture for Ceramic-Matrix Composites; and CERAMIC BULLETIN; Vol. 68, No. 2, 1989.

Bulk structures of the aforementioned three-dimensional weave/knit fabrics are relatively minute three-dimensional fiber structures having an intra-fabric void ratio of 20 to 90% by volume, preferably 30 to 70% by volume, and have the following physical advantages.

(i) Structural material of a composite system in which fiber tips (short fibers) are dispersed in the matrix or a composite in which plural layers are solidified with matrixes using a plane weave/knit fiber fabric as a reinforcing material causes and develops interlayer destruction even by a relatively small force when it is exposed for a prolonged period of time to various external forces such as compressive force, shearing force, impact force and repeated compression/deformation. In the case of a structure in which a composite reinforced with plane cloth is laminated in plural layers, similar destruction occurs and mold strain between the laminate layers causes interlayer cracking and peeling.. Especially, when a stressed state is continued for a prolonged period of time in the living body, interlayer destruction occurs gradually even by a relatively small force during a long period of time. On the contrary, these problems can be solved by the three-dimensional weave/knit fabric structure.

(ii) High strength can be obtained in three-dimensional directions (length, width and height) as a matter of course, and mechanical strength in each direction can also be changed delicately depending on the type of weave/knit fabrics. In other words, a directionality in the mechanical strength can be obtained. This is convenient for matching with the strength of the adjacent biological tissue.

(iii) Since integral forms of continued long fibers can be obtained, a product whose entire portion has extremely high and homogeneous strength can also be formed.

(iv) Physical and chemical properties can be varied by filling the same or different material as matrix in the fabric space. Chemical properties of the matrix material can also be used. In addition, a tissue-connectable area for the invasion of surrounding tissues can be provided making use of continued fabric spaces.

In summary, bulk compatible biomaterials can be obtained which have various advantages in that (1) interlayer peeling does not occur because strength in the through direction can be given, (2) several types of fibers can be hybridized and the fabric space can also be utilized, (3) impact resistance can be improved so that cracking and deformation can be prevented over a prolonged period of time and (4) shapes and dimensional accuracy which cannot be obtained by cross laminating and filament winding methods can be obtained (accuracy of corner angles and taper change in thickness can be effected).

Then, one of the fundamental aspects of the present invention, i.e., "how the three-dimensional fiber architecture (3-DF) satisfy the bulk compatibility including mechanical compatibility and design compatibility", is explained.

The term biomechanical compatibility means that a biomaterial is possessed of mechanical consistency with adjoining or contacting biological tissues. The term mechanical consistency means not the coincidence of their strengths but rather mutual coincidence of their mechanical behavior, especially deformation characteristics. In other words, it means that the stress transferred into biological tissues from a implanted biomaterial or generated therein is maintained within the normal physiological range.

In general, each artificial material shows an elasticity that follows with the Hook's law and a linear elasticity such as viscosity that follows the Newton's law. On the other hand, almost all biological tissues show a nonlinear elasticity, unlike the case of artificial materials. In other words, artificial materials usually show an S-shaped curve as represented by A in the stress-strain curve in FIG. 5, but biological tissues (especially soft tissues) usually show a J-shaped curve like the case of B and also an OB' B" cycle curve having a hysteresis loss. That is, biological tissues are generally possessed of certain properties which cannot be found in conventional artificial materials; namely, (i) they are pseudo-elastic within physiological stress range, and their stress-strain curves under loaded and unloaded conditions do not coincide with each other and (ii) soft tissues such as the skin do not show a linear elasticity and are markedly flexible at a low stress level but become rigid as the stress increases.

In this connection, destruction of a material is divided into "stress destruction" which is generated when the stress exceeds strength of the material and "strain destruction" that occurs when strain by deformation exceeds its limit. Since biological tissues show considerably large deformation before their destruction unlike the case of artificial materials, their evaluation as materials should be made from the viewpoint of compliance which is the inverse of hardness (elastic coefficient) and destruction strain, rather than the hardness itself. In particular, in the connecting area of an artificial material with a biological tissue, it is necessary to design harmonization of strain and conformity of deformability (flexibility) by matching deformation behavior rather than their binding strength.

However, development of artificial biomaterials has been attempted paying attention to a material which has higher apparent strength than that of the living body, from a view point that durability and safety would increase by increasing the strength. Such an attempt to increase durability (strength) usually results in increased modulus of elasticity. That is, as shown by A' in FIG. 5, increased strength results in an S-shaped curve having more large tangent slope and small strain. On the other hand, since biomaterials are strong and flexible materials which have high strength for their low modulus of elasticity (high compliance), it is unavoidable that mechanical incompatibility exists between conventional biomaterials and biological tissues.

What is more, strength and deformation characteristics of a material sharply change not only by the material itself but also by structural designs such as shape of the material body and its composite pattern with different material. In consequence, it is necessary to effect conformity by further considering the bulk compatibility which corresponds to the structure design of biological tissues.

Thus, since high strength and low modulus of elasticity required for biomaterials are contradictory factors in the case of a single material as described above, it is necessary to think a means to satisfy these two factors by composing several materials by imitating the living body.

Biological tissues contain fibers represented by collagen which are arranged in parallel in a certain direction in most cases. FIG. 6 shows conditions of a fiber-reinforced film when it is drawn in various directions against the orientation direction of fibers. As the case of C in the figure, a hard characteristic with a steep slope is obtained when fibers are oriented almost in parallel and the film is drawn in the orientation direction of fibers (FIG. 5C). This is the characteristic of tendon which transfers tensile strength. On the other hand, a weak characteristic with a gentle slope is obtained when drawn in an orthogonal direction to the fiber orientation (FIG. 5D). In the case of a structure which does not show anisotropy like B in FIG. 6, the stress-strain curve shows a downwards convex "J-shaped curve" (FIG. 5B). As the tension increases, fibers start to orient toward the stress direction and the hardness increases rapidly. Since a material having this J-shape characteristic is low in storable elastic energy in comparison with usual linear elastic bodies, it leads to the prevention of accidents such as sudden rupture. In other words, this J-shape characteristic represents mechanical margin as a "safety factor".

On the basis of the above facts, it is indicated that a product having certain strength and deformation property which are close to those of biological tissues will be obtained when a woven/knitted fiber structure is constructed as a biomaterial.

However, since the biological tissue is a three-dimensional structural material, it is necessary for its imitation, as described in the foregoing, to construct not a laminate structure in which two-dimensional fiber reinforcing materials are piled up in the three-dimensional direction, but a three-dimensional fabric structure such as that of the present invention. In addition, forces such as tensile, compression, shearing, bending, twisting, abrasion and the like which will cause breakage and destruction are added to such a structural body from its surrounding biological tissues at various loading rates once or intermittently, statically or dynamically and for a short or prolonged period of time. Therefore, a three-dimensional fabric structure (3-DF) must have variations which can cope with various loading conditions so that it can match with the mechanical behavior of its surrounding biological tissues. It also should have design variations so that it can be made into various shapes at the same time. Such variations as the material of 3-DF can be controlled by changing the type of weave/knit methods, thickness and the number of yarn in each of X, Y and Z axes (degree of filling minuteness of roving, and yarn in the fabric and distribution and arrangement conditions), crossing angles of X, Y and Z axes and the type of yarn knot (knitting) and its strength. As will be shown later in Physical Property Measurement in Example 1-(5), it is evident that the 3-DF of the present invention shows a J-shaped stress-strain curve in XY plane direction and Z axis thickness direction.

Also, modulus of elasticity as the tangent slope of the curve can be changed by the structure of 3-DF and material, degree of filling minuteness and morphology of matrix which is filled, if required. However, it is important that whether these strength and deformation characteristics of 3-DF are really close to those of actual surrounding biological tissues. Practicability of the structure is supported by the curves (FIG. 7 and FIG. 8) of Example 1-(5), because they have compression strength, tensile strength and hysteresis curve which are close to those of the flexible and strong part, for example, intervertebral and other joint cartilages.

The following describes why the 3-DF shows a J-shaped stress-strain curve.

At first, threads slightly loaded with tensile force between knots in the fabric of 3-DF loosens when compression force is added. Twisting of threads at knotting points also loosens. Since resistance at this stage is low and gradually increases with displacement, a curve is obtained which corresponds to a lower portion of Young's modulus as an initial stage of the J-shaped curve. As the compression force is further added, fabric space between knots becomes narrow and the threads finally become a mass and contact each other, and stress increases exponentially. Finally, the structure shows a large compression stress of the thread mass itself. As the result, a J-shaped curve is obtained.

On the other hand, a phenomenon opposite to compression occurs when tensile force is added to 3-DF. In its initial stage, slightly loosened threads between knots are gradually drawn, finally becoming a fully stretched state. Thereafter, twisted threads at knotting points are also knotted hardly, thus becoming a strained state. Until this stage, 3-DF shows a low portion of the curve of Young's modulus. When the tensile force is further loaded, resistance caused by the strain increases exponentially, finally reaching the original stress of the threads and, therefore, stopping the extension. As the result, a J-shaped curve is obtained. As a matter of course, similar behavior can be observed against other stress such as twisting, shearing or the like. When a system is created in which the fabric is connected with its surrounding biological tissues, it functions synchronized with the action of the living body, provided that displacements generated by external forces from the living body are within such a range that the fabric is not damaged or destroyed. In addition, its shape is maintained stably even after extremely large number of repetition. What is more, the degree of the non-damage, non-destruction displacement fox this fabric is larger than the displacement by which a body of a material mass made of a single or composite material becomes unrecoverable due to deformation. Whether the tangent slope of the J-shaped stress-strain curve becomes large or small depends mainly on the degree of roughness/minuteness of the network of 3-DF fabric, namely minuteness of threads, weave/knit method and morphology. However, even in the case of such a system which shows a J-shaped curve, the J-shape usually changes into an S-shape when it is made into a matrix system in which a material is completely filled into the network space, so that it is necessary to pay full attention to the filling mode (ratio, type of material and the like) and morphology when 3-DF of a matrix type which shows a J-shaped curve is desired.

When extremely strong ultra-high molecular weight polyethylene yarn and the like are used in the yarn of 3-DF, breakage of the yarn requires extremely high external forces. In consequence, 3-DF does not break prior to the breakage and destruction of its surrounding biological tissues, so that it has a margin of extremely high safety as a biomaterial from a mechanical point of view. When cells from the surrounding biological tissue penetrate into the fabric space of 3-DF, fill up the space and finally cover up its outer surface, the fabric becomes a part of the biological tissue as a mechanically and physiologically integrated with the biological tissue. Especially, a completely substituted state can be obtained in the case of a 3-DF made of biologically degradable and absorbable fibers such as of poly-lactic acid and the like.

Thus, it was confirmed that the 3-DF is a biomaterial body which satisfies bulk compatibility wherein mechanical compatibility and design compatibility are taken into consideration.

By the way, even in the case of an implant material which is a structural body having a three-dimensional woven/knitted fabric having bulk compatibility, each fiber as its composing unit must have surface compatibility. Accordingly, the following describes about fibers.

Examples of fibers so far used as trial and practical biomaterials include synthetic fibers such as nylon, polyethylene terephthalate, polypropylene, polyethylene (ultra-high molecular weight), polytetrafluoroethylene, polyurethane and the like, natural fibers such as silk, collagen, chitin, chitosan and the like and biologically degradable and absorbable fibers such as poly-glycolic acid, poly-lactic acid, a poly-glycolic acid/poly-lactic acid copolymer, polydioxanone and the like. In addition to these fibers, hydrophilic fibers such as polyvinyl alcohol, acrylic polymers and the like have been studied. As a matter of course, it is possible to use these fibers alone or as a blend yarn thereof in three-dimensionally woven/knitted form for medical purpose.

In this connection, inorganic fibers such as carbon fibers, ceramic fibers, hydroxyapatite and the like may also be used, but not in a desirable mode because of their rigid and fragile properties which result in a technical difficulty in making a three-dimensional woven/knitted fabric structure and an aptness to form many debris due to breakage of fibers at the time of weaving, as well as a possibility of generating foreign body reaction after implantation in the living body because of the aptness to form and release fiber debris. In consequence, it is desirable to select a base material for a three-dimensional woven/knitted fabric of a matrix system of organic fibers or similar biocompatible polymers and ceramics.

Fibers are divided into staples and filaments and, in any case, they are used as one yarn unit for weaving as they are or, when a thread is too thin, after tying up several threads in a bundle and twisting them to make a thick yarn. However, there is a limit in desirable thickness, because apparent rigidity becomes high when the yarn is too thick, thus making the weaving difficult. Therefore, thin threads are used by tying them up in a bundle in most cases. However, when the staple-composing thread unit is too thin fibers, the threads become loose and cause disadvantageous hairiness at the time of the three-dimensional fabric processing and during a prolonged period of stressed time in the living body. In such cases, deterioration of physical properties and physical stimulation upon surrounding tissues are probable. Accordingly, filaments having an appropriate thickness are rather desirable.

The aforementioned organic fibers can be classified into (i) bioinert fibers such as polyethylene, polypropylene and polytetrafluoroethylene, (ii) bioaffinitive fibers such as polyurethane, polyvinyl alcohol, acrylic polymers, silk, and the like and (iii) biocompatible and biologically degradable and absorbable fibers such as collagen, chitin, chitosan, poly-glycolic acid, poly-lactic acid, poly-glycolic acid/poly-lactic acid copolymers, polydioxanone and the like. The bioinertness, bioaffinity, biocompatibility and biological degradability and absorbability described above are defined in D. F. Williams "Progress in Biomaterial Engineering, 4 Definitions in Biomaterials" (1987) (Elsevier).

Since a three-dimensional fiber base material in which the fiber belonging to (i) is used is biologically inert, it is useful for an implant material which is present in the living body for a prolonged period of time. On the other hand, the fiber of (ii) has bioaffinity but with no decisive proof of not causing generation of damages when implanted for a prolonged period of time, so that it is necessary in some cases to reoperate for removal when the object is achieved. Since the fiber of (iii) is degraded and absorbed sooner or later, it can be applied to a part where regeneration of the biological tissue is possible.

These fibers are used properly according to their characteristics. Though not only (i) but also (ii) and (iii) have no bioactivity. Thus, it is also necessary to produce fibers (iv) which can provide a chance and area of connectivity with tissues, namely fibers to which bioactivity (tissue connectivity) is endowed by physically and chemically modifying the surface of the fibers of (i), (ii) and (iii). A fabric structure made of the fibers (iv) is one of the important objects of the present invention. Especially, a fabric structure made of the fibers (i) and (iv) is required in the case of an implant material which is implanted for a prolonged period of time.

That is, unlike the case of surgical suture which is used in a small quantity and does not require long-term durability, biocompatibility of whether biologically inert or active is an essential condition to avoid foreign body reaction of the living body as described in the foregoing when the fabric structure is used for the purpose of filling, prosthesis, substitution and the like of damaged parts of the living body, where various cubic shapes, respective volume and long-term durability (no deterioration) are required. Long-term durability means no chemical and physical (mechanical) deterioration. Though a large number of fibers, especially synthetic fibers, have higher strength than biological tissues and have been attempted to be used in implants, they are not worthy of applying to a long-term implantation because of their insufficient biocompatibility and insufficient mechanical durability due to deterioration in the living body. An excellent implant which has mechanical margin, long-term durability and biocompatibility at the same time can be obtained by the use of a three-dimensional structure of inert synthetic fibers, especially those having high strength that can withstand extreme load unexpectedly added to the living body and having modified surface to give biological activity. In that case, tissues around the implant gradually penetrate into fabric space of the three-dimensional woven/knitted fabric and are three-dimensionally intertwined with the fibers. Accordingly, only chemical bonding but also strong physical bonding can be obtained. Under certain circumstances, surrounding tissue covers up the three-dimensional fiber structure for such a prolonged period of time that the structure can adapt itself to the surrounding tissue. At such a stage, structural morphology of the three-dimensional woven/knitted fabric becomes useful for the synchronization of mechanical stress with the surrounding tissue.

In contrast, it is necessary in some cases to definitely inhibit foreign body reaction for a long period of time, by modifying the surface of fibers to obtain more inert property.

Surface modification can be effected by various means such as chemical methods, physical methods and combinations thereof which are described, for example, by Yoshito Ikada in "Principle and Application of High Polymer Surface" (1968), Kagaku Dojin. When classified from the view point of plastic surface treatment methods, they are divided into (A) dry treatment and (B) wet treatment. The treatment (A) includes discharge treatment (corona discharge and glow discharge), flame treatment, ozone treatment, ionized ray treatment (ultraviolet ray, radiation and electron beam), rough surface treatment, polymer blend (different polymers and filling of inorganic substance) and the like, and (B) includes chemical agent treatment, primer treatment, polymer coating, electrodeposition, catalyst-aided graft and the like.

In general, a change which first occurs when a material is implanted in the living body is adsorption of protein to the material surface, followed by adhesion of cells. The adsorption of protein to the material surface is greatly influenced by chemical structure, surface charge, hydrophilic property, hydrophobic property, micro phase separation and the like of the material. Especially, "water wettability" of the material surface is an important characteristic for the adhesion of cells, which is a proof that van der Waal's force is dominantly present between cells and the material. Since it is known that a highly hydrophilic surface of 40° or less in contact angle generally has a small number of adhered cells and a small possibility of causing foreign body reaction, modification of such a highly hydrophilic surface by any one of the aforementioned surface treatment methods is an effective means for obtaining a biocompatible surface. For example, fixation of a hydrogel or the like is an effective means for obtaining an extremely hydrophilic surface. The hydrogel to be used may be either a natural polymer gel or a synthetic polymer gel. The natural polymer gel is divided into polysaccharides and proteins, and examples of such polysaccharides include methylcellulose, hydroxypropylmethylcellulose, alginic acid, agar, carrageenan, proteoglycan, hyaluronic acid and the like and the protein includes gelatin, fibrin, collagen, casein and the like. Examples of the synthetic polymer gel include those of polyvinylalcohol gel, polyethyleneoxide gel, polyhydroxymethacrylic acid gel (Poly-HEMA) and the like. These gels may be optionally selected depending on the type of fibers to be used in the three-dimensional fabric, the area to be implanted and the shape of the implant material.

The following illustrates methods for obtaining bioactive surfaces.

That is, it is necessary to add a certain quantity or more of charge to the surface of a material for the growth of cells on the material surface. In other words, a certain degree or more of $\zeta$ electric potential is required. This is attained by a method in which an anionic or cationic dissociation group is fixed on the surface of a polymer material.

Also, since bioactive inorganic bioglass, alumina wallastonite glass ceramics (to be referred to as AW or AW glass ceramics, hereinafter), hydroxyapatite and the like are available as materials for hard tissue use in the field of plastic reconstructive surgery, a material capable of binding to the living body can be produced by a method in which these bioactive materials are blended with a polymer and coated on the surface of fibers, in which the surface is scraped after covered with a coating polymer to expose these ceramics or in which fine powder of these ceramics is sprayed to the fiber surface which is slightly softened by heating, with a portion of the powder particles being exposed on the surface. As an alternative method, a material capable of inducing bone tissue can be produced by introducing phosphate groups to the surface of a polymer.

A method in which a natural biomaterial such as collagen, gelatin, fibronectin, hyaluronic acid, heparin or the like is fixed on the material surface making use of the aforementioned surface treatment method is one of the effective methods for the purpose of producing a material which can bind sufficiently with soft tissues such as connective tissues.

In addition to the above methods, many techniques can be devised for various purposes, such as fixation of thrombomodulin which is a typical protein that inhibits blood coagulation on blood vessel endothelial cells, formation of thin film of hydroxyapatite on the surface, fixation of an enzyme such as urokinase and the like, and fixation of growth factors, growth hormones and the like.

Three-dimensional woven/knitted fabric structures of organic polymer fibers having the aforementioned surface characteristics have surface biocompatibility and bulk biocompatibility. In addition, they can be used as biomaterials which have such enough mechanical durability and tissue connectivity that they can withstand long-term implantation.

Next, typical examples of the implant material of the present invention are described in the following.

[I] A case in which ultra-high molecular weight polyethylene (UHMWPE) fibers are made into a three-dimensional fabric structure Essentially bioinert polyethylene fibers are obtained by so-called gel spinning in which ultra-high molecular weight polyethylene having a molecular weight as UHMWPE of at least 1,000,000, preferably about 3,000,000 to 5,000,000, is dissolved in decalin or a paraffinic solvent, the resulting dilute solution is discharged from a nozzle of a spinning machine into a cooled water bath to spin the thus gelled product into fibers and then the solvent is removed. The ultra-high molecular weight polyethylene fibers vary within the range of from 100 to 1500 denier (10 to 150 filaments), of which a thickness of from 500 to 1000 deniers are preferable. When too thick fibers are used, production of a three-dimensional woven/knitted fabric structure becomes difficult due to high rigidity, while too thin fibers are apt to be loosened into filament units during the fabric structure production. Strength of such ultra-high molecular weight polyethylene fibers, such as "Techmiron" manufactured by Mitsui Petrochemical Industries, Ltd. is 35 g/denier in specific strength and 1160 g/denier in specific modulus of elasticity, and these values are larger than the respective values of 28 g/denier and 1000 g/denier of the aramide fibers which are considered to be the most strong fibers (data obtained from Mitsui Petrochemical Industries, Ltd.). In consequence, breakage can be prevented even when an unexpectedly excess force is loaded. The following three-dimensional fabric structures suitable for implants can be produced using such fibers.

(1) A three-dimensional fabric structure comprising minute orthogonal fabric, non-orthogonal fabric or leno fabric in the shape of plate, cylinder, rod, block or other irregular shape is produced using 500 to 1000 denier yarn. This structure can be used directly as an implant in the form of a bioinert artificial bone or the like for filling, prosthesis or substitution of damaged parts in the living body, but penetration of surrounding tissues into spaces between fibers and in the three-dimensional fabric and subsequent binding cannot be expected because of the inertness of the yarn.

(2) By grafting the surface of the yarn of (1) with a monomer or oligomer having an organic phosphate group such as methacryl(poly)oxyethyl phosphate or the like, bioactive UHMWPE fibers having bone-bindable surfaces are obtained. By making such fibers into a three-dimensional fiber architecture in the same manner, a three-dimensional fabric structure is obtained which has such a function that surrounding tissues can penetrate into spaces between each filament and in the fabric. The graft treatment may be carried out after producing the three-dimensional fabric. This structure may be used not only as an artificial intervertebral disk, an artificial root of tooth and the like which require binding with bones. By creating a three-dimensional body by means of braiding, namely, by means of braid techniques to obtain a cubic or irregular shape, this structure is also used as an artificial tendon, an artificial joint and the like which can partly (end portions) bind to the surrounding bone, which is a function that cannot be attained by conventional polyester or polypropylene.

(3) The surface of the yarn of (1) is coated with a melted low density polyethylene (LDPE, LLDPE or VLDPE) and made into a three-dimensional fabric in the same manner. Similar to the case of (1), this structure can avoid possibility of causing loosening of the yarn-constituting filaments during its long-term use. A surface treatment like the case of (2) can also be effected and, in such a case, physical strength of the multifilament of UHMWPE as the core is not spoiled by the surface treatment. Another advantage is that thermoformability of the polyethylene used for the coating can be utilized. That is, since the fabric produced from the UHMWPE filaments coated with a low density polyethylene has a void ratio of around 50%, the fabric can be thermoformed in an appropriate mold at a temperature of lower than the melting point of UHMWPE and higher than the melting point of the low density polyethylene to obtain a molded body which is reinforced with fibers in three-dimensional directions, does not generate interlayer peeling and can be used for filling, prosthesis and substitution of damaged parts in the living body. In this case, a molded body in which the void is remained can also be obtained by adjusting the degree of compression and the degree of thickness of the coating.

(4) The low density polyethylene of (3) is mixed with bioactive materials, namely bioglass, ceravital, synthesized hydroxyapatite (HA) and AW glass ceramics (AW•GC), and the mixture is melted and coated on the UHMWPE fibers. The surface is scraped off to expose a portion of particles of the aforementioned bioactive materials on the surface. The fibers are made into a three-dimensional fabric similar to the case of (1). When this fabric body is soaked in a simulated body fluid at 37° C., a large number of HA crystals accumulate on the yarn surface using the crystal of the bioactive material as the nucleus. Since this fact supports that such a three-dimensional fabric body induces a bone in the living body (in the bone), and the bone penetrates into the fabric space and covers its surface, such a structure is useful as an artificial intervertebral disk, an artificial bone, an artificial mandibular bone, an artificial root of tooth and the like which require long-term physical durability.

In this connection, it is possible as a matter of course to provide bioaffinity to the surface of fibers (yarn) of the three-dimensional fabric body of (1) or (3) by the aforementioned surface treatment method. Also, coating of the low density polyethylene on the UHMWPE fibers may be effected via an adhesive agent or by irradiating the coated body with γ rays of about 2.5 M rad or less to form loose crosslinking.

[II] A case in which high strength polyvinylalcohol (PVA) fibers are made into a three-dimensional fabric structure High strength PVA fibers have a specific strength of 17 to 22 g/denier which is fairly high. Using the fibers of 500 to 1000 denlet, a minute fabric body is woven up in a three-dimensional complex shape such as of elbow and shoulder joint, hip joint head or the like. This fabric body is put into a mold slightly larger than the woven fabric body having a shape of respective joint, and aqueous solution of PVA is poured into the mold. By subjecting to repeated freeze-thawing, a fiber fabric body filled and coated with a gel having a hardness of cartilage is obtained.

This gel has high mechanical strength, is useful in water resistance (elution) tests and chemical and biological tests as a medical material and can be sterilized with γ rays. Though the gel itself cannot withstand sewing, strong sewing can be obtained safely because of the high strength PVA three-dimensional fabric structure in the gel. In addition, since it is possible to sew it on a metal part as a portion of cartilage of the bone head of an artificial joint and then filling the PVA gel to mold a gel body, it has a great advantage in solving the desired object, i.e., connection of metals and ceramics with organic materials, especially, different materials which are difficult to adhere (e.g., organic bodies, especially gels). This structure is also useful for the prosthesis and filling of deleted parts in the living body as a mandibular deficiency filling body and the like.

[III] A case in which biologically decomposable and absorbable poly-L-lactic acid (PLLA) fibers are made into a three-dimensional fabric structure (1) As one of the biologically decomposable and absorbable aliphatic poly-α-esters, PLLA which is degraded relatively gradually and shows mild biological reactions is mixed with unsintered hydroxyapatite (HA). That is, HA and PLLA are mixed in chloroform to dissolve PLLA, the solvent is evaporated completely and then the residue is pulverized. This is thoroughly dehydrated and degassed using a plunger type extruder and melt-extruded in vacuo to obtain yarn of 0.3 to 0.5 mmϕ. Using this yarn, a three-dimensional body of orthogonal fabric or non-orthogonal fabric is woven in the shape of a plate or a block.

When such a structure is implanted in the living body, PLLA on the surface of the yarn is gradually decomposed by the body fluid and the filled HA therefore appears on the surface. Using this HA as a nucleus, crystals of HA further grow in the body fluid. It is considered that, as the decomposition of PLLA progresses, inner HA is exposed and gradually substituted by HA crystals and finally displaced by HA crystals almost completely, thus becoming an HA body close to the original shape of the plate or block. In consequence, such a structure is useful for the filling and prosthesis of a bone to fill up a deficient part of the bone. Since such filling material and prosthetic material are initially three-dimensional fabric structures of yarn, they have a strength which is higher than those of bones in the living body. When substituted by HA crystals, the structure loses its strength temporarily as an assembled body of crystals, but stress on its surrounding tissue disappears at the same time and thereafter the structure takes a step to be assimilated to the biological bone, which are convenient for the bone growth and stress shielding.

(2) The three-dimensional fabric structure of UHMWPE coated with the low density polyethylene of [I]-(3) is soaked for a short time in a hot methylene chloride solution of AW and PLLA and then dried. Since hot methylene chloride swells and dissolves the low density polyethylene, the AW/PLLA system adheres properly to the surface in the form of thin film or fine particles.

When this structure is used as a prosthetic or filling material of a deficient part of a bone, the bone tissue penetrates and fills the structure surface like the case of (1), and the structure is finally connected well with its surrounding bone. At this stage, initial strength of the UHMWPE fibers as the core material of the yarn of the three-dimensional fabric body remains unchanged. Accordingly, unlike the case of (1), it can be applied suitably to a part where strength is required. Required shapes can be woven optionally as three-dimensional fabric bodies.

[IV] A case in which collagen fibers are made into a three-dimensional fabric structure Collagen fibers are woven into a relatively rough three-dimensional leno fabric in the shape of a block. Unsintered hydroxyapatite (HA) is mixed in a gelatin solution, and the HA/gelating conc. solution is filled in a mold having a slightly larger than the fabric body. After thoroughly drying, a collagen three-dimensional fabric structure coated with HA/gelatin is obtained. In this case, it is favorable to effect crosslinking using a crosslinking agent such as formalin, glutaraldehyde, diepoxy compound or the like, since proper adhesion to collagen fibers can be attained and the structure is not easily dissolved by the body fluid but swells to form a hydrogel, so that HA powder does not flow out.

This block has similar effects to those of [III]-(1) and is useful for prosthesis and filling of deficient portions of bones, particularly cartilages. Similar effects can be obtained when HA is changed to AW. In the case of AW, when the PLLA of [III] is deteriorated by hydrolysis and the hydrolyzed product generates an acidic atmosphere, it could prevent accumulation and growth of HA crystals from the living body. However, such a phenomenon does not occur when collagen fibers are used, which is advantageous.

[V] A case in which other fibers are made into a three-dimensional fabric structure Polypropylene fibers, acrylic fibers or polyester fibers are woven and knitted into a shape such as a plate, a block, a rod, a cylinder or the like or other optional shape such as a shape of a joint or its deficient part. Each of these products is subjected to plasma surface treatment, soaked in a hyaluronic acid solution or a gelatin aqueous solution and then subjected to crosslinking in the similar manner to the procedure of [IV] to obtain a shaped body. By the crosslinking, binding of the hydrogel to the fibers is obtained and dissolution of the hydrogel into water is prevented. In addition, adhesion between the fibers and the gel is improved by the plasma treatment.

Unlike the case of [IV], these fibers are not biologically degradable and can maintain their strength in the living body for a prolonged period of time. Because of this feature, these structures are useful as substitutes of biological tissues which should maintain strength for a prolonged period of time. Since they are cubic forms of dense fiber fabric, their connection with surrounding tissues by the yarn can be made, so that their development as a joint cartilage can be made. In addition, mixing of these structures with unsintered HA, AW, bioglass, delimed bone or BMP (bone morphogenetic protein) can be used as base materials by which enhancement of the induction and formation of a bone can be expected.

Effects

The implant material of the present invention uses as its base material a bulk structure which comprises a three-dimensional woven or knitted fabric of organic fibers or a composite fabric thereof. Therefore, it is free from a problem of causing interlayer destruction which is found in a composite in which fiber tips (short fibers) are dispersed in its matrix or which is found in a composite in which several pieces of plane woven/knitted fabric of fibers are piled and fixed with a matrix. It also has high strength in three-dimensional directions and, depending on the woven/knitted fabrics, and it has synchronization with the strength of biological tissues in delicate response to the mechanical strength in each direction of the fabric. In addition, since the material has a space in its fabric, it can be connected to its surrounding tissue through penetration of the biological tissue into the space and it also can be provided with variation of physical and chemical properties by filling the space with a matrix of the same or different material. What is more, this bulk structure has surface biocompatibility such as bioinert property and bioactive property, in addition to the aforementioned mechanical biocompatibility and structural design compatibility, so that it does not cause foreign body reaction or can be implanted in the living body for a prolonged period of time through its connection with biological tissues.

BEST MODE OF CARRYING OUT THE INVENTION

Figure 1:
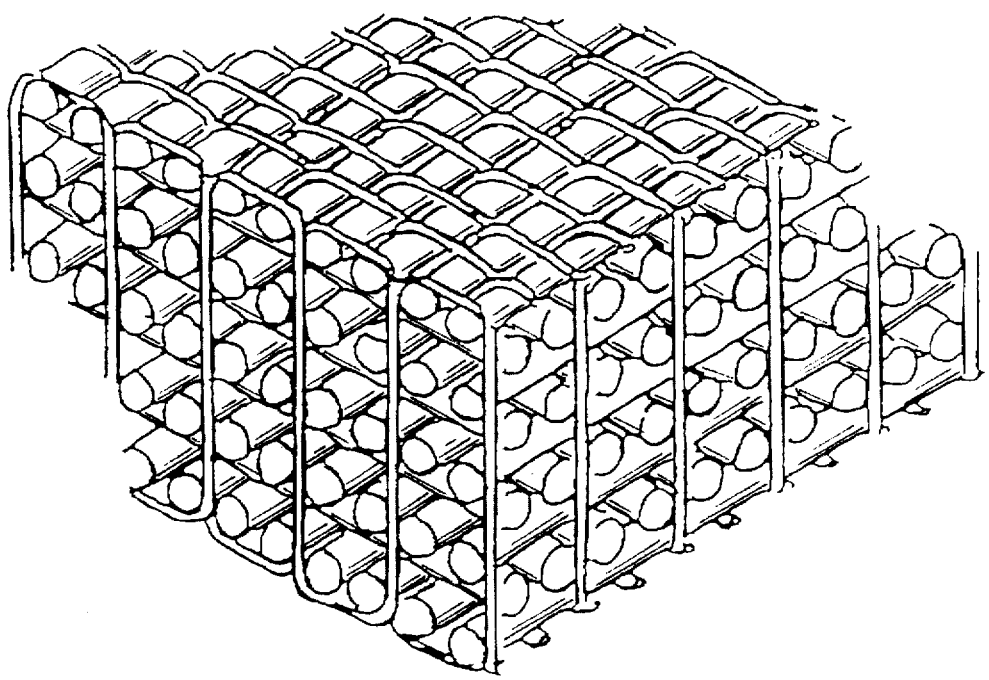
FIG. 1 is a conceptional drawing of an orthogonal fabric.
Figure 2:
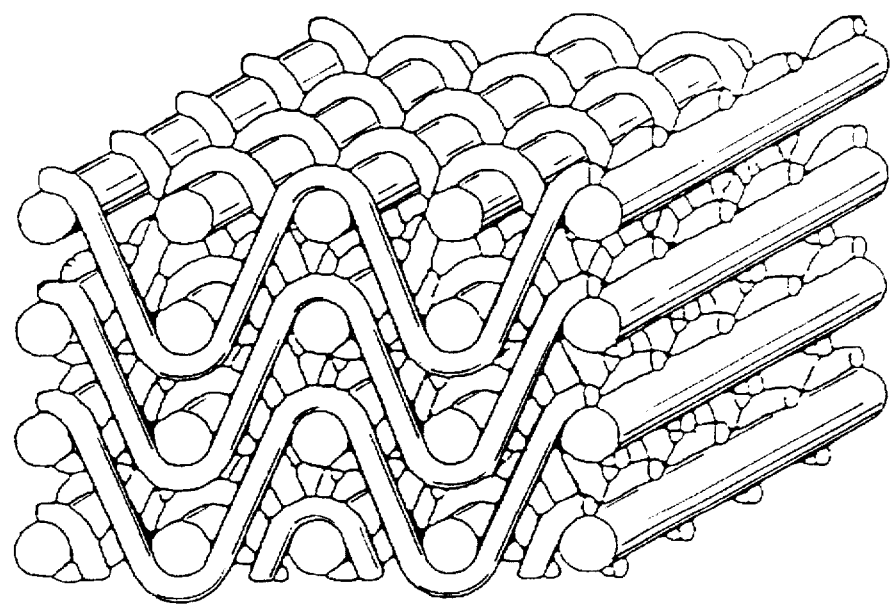
FIG. 2 is a conceptional drawing of a non-orthogonal fabric.
Figure 3:
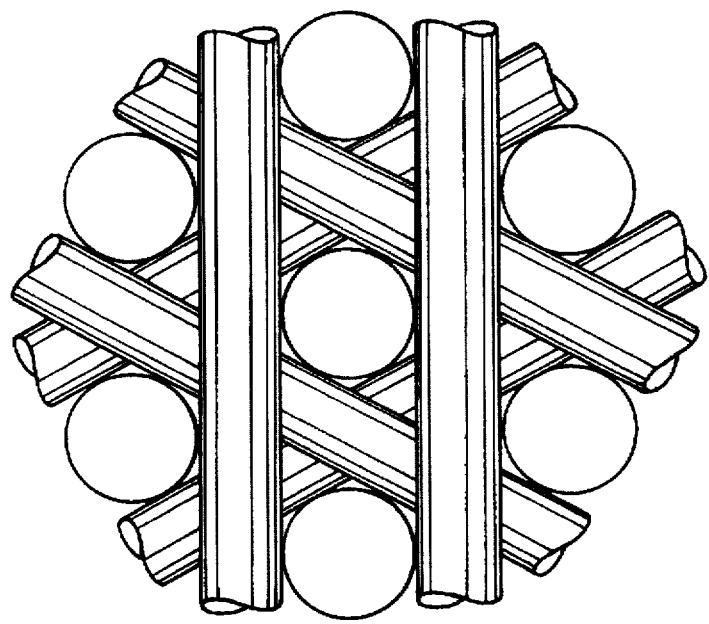
FIG. 3 is a conceptional drawing of a tetra-axial fabric and FIG. 4 is a conceptional drawing of a penta-axial fabric.
Figure 4:
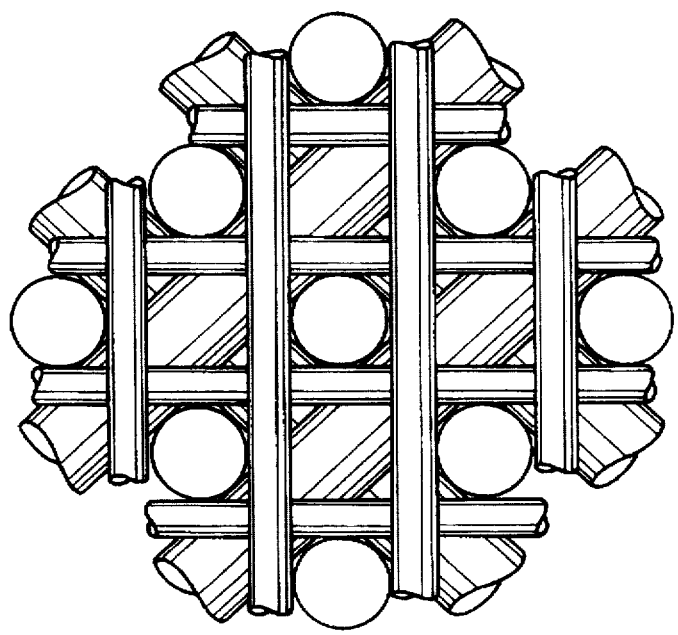
Figure 5:
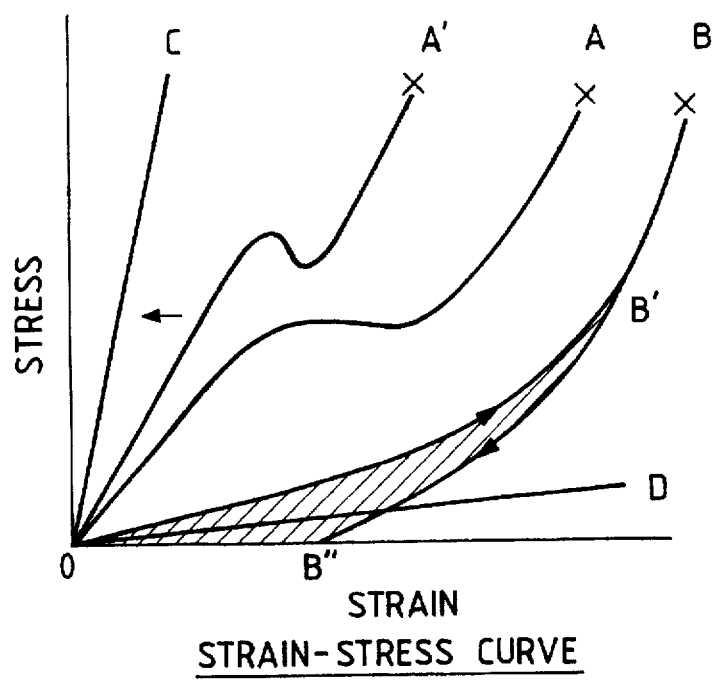
FIG. 5 is a graph showing stress-strain curves of artificial materials and biological tissues.
Figure 6:
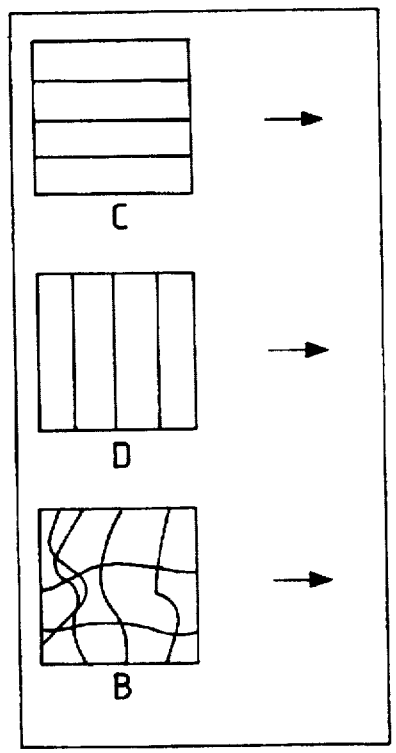
FIG. 6 is a graph showing orientation direction and tensile force of fibers.

Examples of the present invention are described in the following.

[Example 1] A case of three-dimensional fabric structure of ultra-high molecular weight polyethylene (UHMWPE) fibers (1) "Techmiron" manufactured by Mitsui Petrochemical Industries, Ltd. as a yarn of 500 denier (50 filaments) was treated with a hand operating practice machine constructed for this purpose to produce a three-dimensional fabric structure of a block-shaped orthogonal fabric in a size of length×width×height=50.4×35.8×13.3 mm, consisting of 24 yarns as the X axis, 35 yarns as the Y axis and 900×2 (2 means folding) yarns as the Z axis and 46 layers of laminates, with an orientation ratio of axes (weight ratio or yarn length ratio) of X:Y:Z=3:3:1. This structure was relatively soft, because it was produced by loosening tightness of the twisting of knots so that minuteness of the fabric became not so high. This structure can be used directly as a filling, prosthetic or substitution material in the form of a biologically inert artificial bone (cartilage). However, since surrounding tissues cannot penetrate into fiber space and three-dimensional fabric space and bind therewith, it may be applied suitably to a part where their binding must be avoided (e.g., a joint).

(2) A low density polyethylene (LLDPE: Idemitsu Polyethylene L grade $\overline{Mw}$=84,000, manufactured by Idemitsu Petrochemical Co., Ltd.) was melted at 120° C. and coated on the surface of the same yarn of (1) in an average thickness of 85 μm to prepare a yarn of 400 μm in average diameter. By this treatment, it was able to avoid loosening of the yarn even after loading of shearing force for a prolonged period of time. Next, this yarn was subjected to 5 seconds of plasma treatment in an atmosphere of 0.04 Torr Ar gas. Thereafter, the plasma-treated yarn was soaked in a solution of methacryl oxyethylene phosphate and, after degassing and sealing in a box, exposed to ultraviolet rays at 35° C. for 1 hour to graft phosphate groups on the surface of the yarn. Using this yarn, a three-dimensional fabric structure of a block-shaped orthogonal fabric in a size of length×width×height= 50.3×35.4×15.6 mm, consisting of 24 yarns as the X axis, 35 yarns as the Y axis and 900×2 yarns as the Z axis and 69 layers of laminates, with an orientation ratio of axes of X:Y:Z=3:3:2 was obtained by the similar manner as in (1). The structure was considerably hard in the Z axis direction, because the yarn was thicker than (1) and the weaving was carried by strongly tightening the Z axis. This structure was then soaked in an aqueous solution of calcium chloride and orthophosphoric acid ([Ca] =20 mM, [PO$_4$]=16 mM, pH=7.4) to effect formation of a thin layer of calcium phosphate on the surface of the yarn. Since this three-dimensional weave has of a connectivity to bone tissues, it is useful especially for the filling, prosthesis and substitution of deficient parts of bones.

(3) The LLDPE-coated UHMWPE yarn of (2) was used to produce a three-dimensional weave of a block-shaped orthogonal fabric in a shape of length×width×height=50.3× 35.5×16.5 mm which was softer than (2) and had the same X, Y and Z numbers, laminate numbers and orientation numbers as those of (2). This weave was put into a metal mold of 50 mm in length and 35 mm in width and compressed in a thickness of 14 mm by pressurizing it from the upper side at 125° C. which was lower than the melting point of UHMWPE and higher than the melting point of LLDPE. Since the resulting product is fairly harder than the block body of (2), it is useful as a part where a hardness of cortical bone is required.

After softening the surface of this fabric structure by heating, to this was sprayed fine particle powder of AW glass ceramic which has been passed through a 300 mesh screen. It was confirmed by microscopic observation that about 70% or more of the surface area was covered with the powder. Exposure of the powder form the surface was also confirmed.

(4) A low density polyethylene (Petrosen, grade 352, Mw=94,000, manufactured by Toso Corp.) was melted and mixed with fine particle powder of a bioactive ceramic, i.e., unsintered hydroxyapatite (HA), which has been passed through a 500 mesh screen, in a volume ratio of LDPE/HA= 1/1, and the mixture was cooled and pulverized to obtain a flake-shaped composite body. This composite body was again melted and coated on the same UHMWPE yarn as that used in (1) to obtain a yarn of 500 μm in average diameter. Its surface was scraped off to obtain a yarn of 400 μm in average diameter. It was confirmed that a portion of the HA particles was exposed partially on the surface. Using this yarn, a three-dimensional weaving having the same size of (2) was produced.

When these three-dimensional fiber structures of (3) and (4) were soaked at 37° C. in a simulated body fluid having a composition of NaCi: 8 g/l, NaHCO$_3$: 0.35 g/l, KCl: 0.22 g/l, K$_2$HPO$_4$: 0.17 g/l, MgCl$_2$•6H$_2$O: 0.5 g/l, CaCl$_2$•2H$_2$O: 0.37 g/l, Na$_2$SO$_4$: 0.07 g/l, HCl: 41 ml/l and tris (hydroxymethyl)aminomethane: 6 g/l, it was confirmed that crystals of HA grew after 1 to 2 weeks using these bioactive ceramics as the crystal nuclei and covered the surface of the yarn. Since this fact means that these fabric bodies induce bone and connect strongly with their surrounding tissues via penetrating collagen fibers, they are useful especially for the filling, prosthesis and substitution of deficient bones which require strength for a long period of implantation.

(5) a) The same yarn of (1) having a thickness of 300 denier (30 filaments) was coated with the same LLDPE of (2), and the thus prepared yarn of 300 μm in average diameter was used for the production of a relatively soft semielliptic three-dimensional weave (similar to the shape of intervertebral disk) in a size of length×width×height=50× 35×12 mm, consisting of 24 yarns as the X axis, 35 yarns as the Y axis and 730×2 yarns as the Z axis and 55 layers of laminates, with an orientation ratio of axes of X:Y:Z=3:3:2.

b) Also produced was a rectangular rod-shaped three-dimensional fabric structure in which the X and Y axes are arranged in an oblique angle of 45° to the Z axis, in a size of length×width×height=105×15×13 mm, consisting of 24 yarns×26 layers as the V axis, 35 yarns×26 layers as the W axis (called V axis and W axis because of the oblique angle) and 1400×2 yarns as the Z axis, with an orientation ratio of axes of V:W:Z=3:3:1. Since this structure has an oblique angle, it can be stretched and contracted in each axial direction. This is also a soft fabric structure which can be easily bent especially in the VZ and WZ planes.

Thus, a) indicates that even a semielliptic irregular form can be woven, and b) indicates that orientation in stretching and contracting function, bendability and strength can be provided by changing the crossing of yarns to an unorthogonal angle.

In consequence, when portions of a) and b) where fibers are to be connected with biological tissues are treated with a bioactive ceramic similar to the case of (3) and (4), they are useful as filling, prosthesis and substitution of artificial cartilages such as an artificial menisci, an artificial intervertebral disk and the like which require cartilage-like mechanical properties so that they can bind strongly to the surrounding biological tissue and follow its movement.

Figure 7:
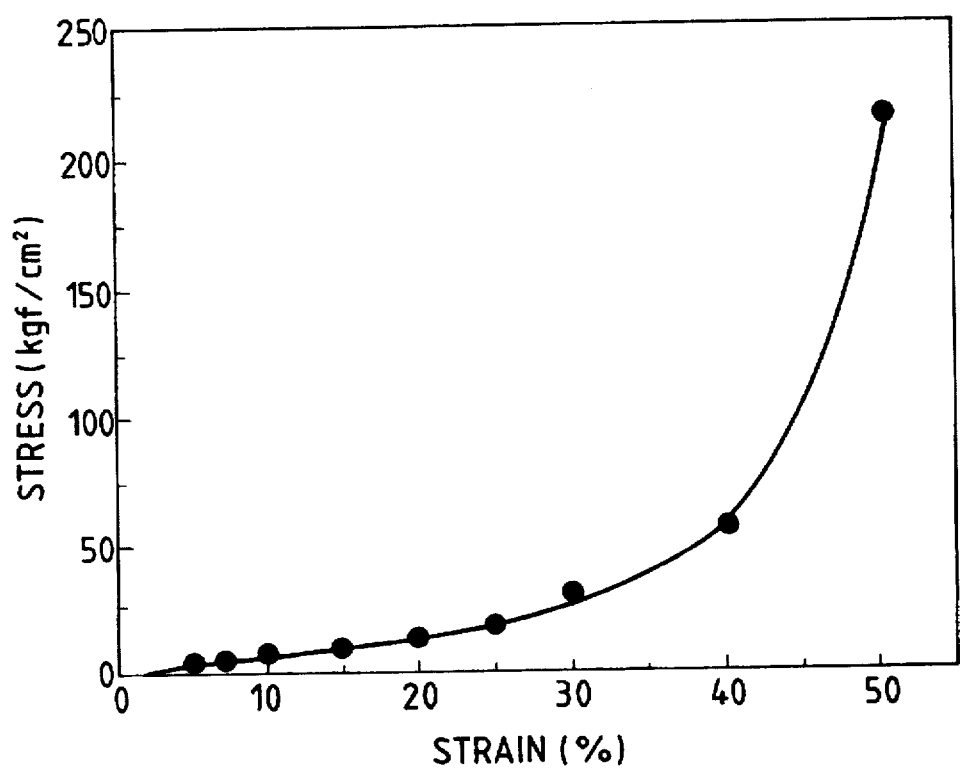
FIG. 7 is a graph showing a stress-strain curve of a three-dimensional fiber fabric structure as an example of the present invention.
Figure 8:
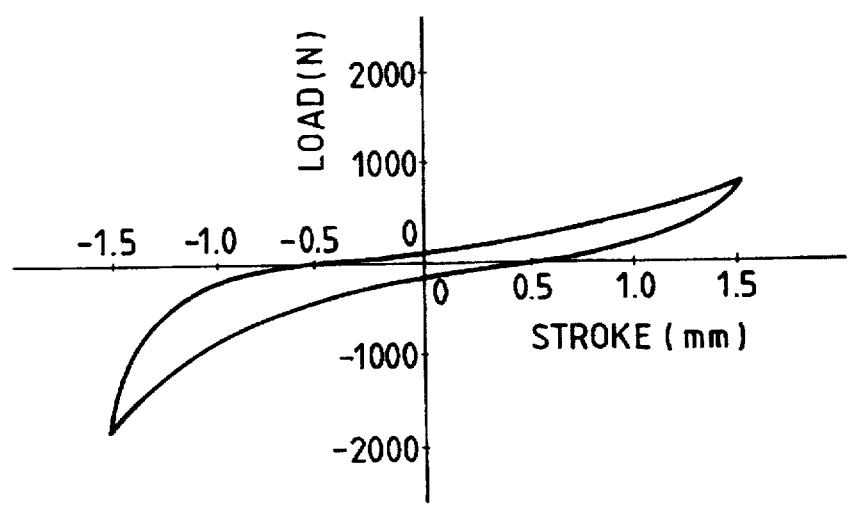
FIG. 8 is a graph showing a compression-tensile hysteresis-loss curve of a three-dimensional fiber fabric structure as an example of the present invention.

In this connection, a compression stress-strain curve in the Y axis direction of the XY plane of (5)-a) and a hysteresis curve of compression-tensile (load-stroke curve) are shown in the following figures. This physical property was measured using a servo pulser [manufactured by Shimadzu Corp.] (FIGS. 7 and 8).

Since these structures show a J-shaped curve which is quite close to the deformation properties of joint cartilage tissues in the living body, their practicability is supported.

[Example 2] A case of polyvinylalcohol (PVA) fibers

Using fibers (1500 denier/300 filaments) having a high strength (17.1 g/d) prepared by gel spinning of a polyvinylalcohol (PVA) and a polymerization degree of 4,000, a three-dimensional complex shape body of oblique (45°) fabric having a shape of patera (hemisphere form of 20 mm in diameter and 7 mm in height) was produced. Pitch of its Z axis was about 2 mm. This fabric body was put into a mold having a slightly larger size than the fabric body, and into the mold was further added an aqueous solution containing about 20% of PVA having a saponification degree of 98 to 99.9% and a polymerization degree of 2500. This was subjected to freeze-thawing treatment (thawing temperature, 0° C. to room temperature) 9 times (freezing time, 4 hours) to obtain a fiber fabric body filled and coated with a gel of a cartilage-like hardness, having a water content of 85% and a modulus of elasticity E' of 2 to 3 [$10^5/Nm^2$].

[Example 3] A case of biologically degradable and absorbable poly-L-lactic acid (PLLA)

(1) PLLA having a viscosity average molecular weight $\overline{M}v$ of 200,000 was mixed with 300 mesh screen-passed particles of unsintered hydroxyapatite (HA) (Ca/P=1.67) in a weight ratio of 4:1 in such amounts that total concentration of HA and PLAA in chloroform became 4%. After dissolution of PLLA, the solvent was completely evaporated and the residue was pulverized. This was thoroughly dehydrated and degassed using a plunger type extruder and melt-extruded in vacuo to prepare a yarn of 0.6 mm$\phi$. This yarn was used to produce a cubic three-dimensional fabric body of orthogonal fabric in a size of length×width×height=10× 10×10 mm, consisting of 15 yarns×22 layers as the X axis, 15 yarns×22 layers as the Y axis and 127×4 yarns as the Z axis, with an orientation ratio of 2:2:3.

When this was implanted in the living body for a half year to a year, PLLA of the surface of the yarn decomposed gradually by the body fluid and the filled HA appeared on the surface. Using this HA as the nucleus, HA crystals from the body fluid grew. In consequence, this is useful as a scaffold in which it remains its strength in the living body until PLLA is decomposed and then disappears to be displaced by the biological bone.

(2) The three-dimensional fabric structure of LLDPE-coated UHMWPE produced in Example 1-(2) was soaked in a hot methylene chloride solution containing 7 wt % of AW and PLLA as a total amount with a AW/PLLA weight ratio of 1:1 for 60 minutes and then dried (AW was used as 200 mesh screen-passed fine powder and PLLA was the same as (1)). Since hot methylene chloride swells and dissolves LLDPE, the AW/PLLA system adhered well on the surface as fine particle form.

When this was used as a prosthetic or filling material of a deficient part of bone, its surface was displaced by the biological bone in parallel with the decomposition and disappearance of PLLA and finally connected well with the surrounding biological bone. At this stage, the initial strength of UHMWPE as the core of the yarn of the three-dimensional fabric body remained unchanged.

[Example 4] A case of collagen fibers

Collagen fibers of 700 denier were prepared for trial and three-dimensionally woven into a block body of relatively rough orthogonal fabric similar to the case of Example 3. To a mold having a slightly larger size than this shape was filled a conc. solution prepared by mixing 5% aqueous solution of gelatin with unsintered hydroxyapatite (HA) powder having a 200 mesh screen-passed particle size, with an HA/gelatin weight ratio of 1:1 and in a total HA/gelatin amount of 40 vol %. Thereafter, this was thoroughly dried to obtain a collagen three-dimensional fabric structure covered with HA/gelatin. In this caser when crosslinking is effected using glutaraldehyde as a crosslinking agent, proper adhesion to collagen fibers can be attained and the structure is not easily dissolved by the body fluid but swells to form a hydrogel, which is favorable since HA powder does not flow out.

This block showed similar effects to those of Example 1-(5) and is useful for prosthesis and filling of deficient portions of bones, particularly cartilages. When PLLA is deteriorated by hydrolysis and the hydrolyzed product generates an acidic atmosphere like the case of Example 3, there may be a problem that accumulation and growth of HA crystals from the living body are prevented. However, this Example has an advantage that such problem does not occur.

[Example 5] A case of polyester fibers

Polyester fibers of 300 denier were woven into an oblique (45°) fabric having a trapezoid section (6 mm in longer side, 3 mm in shorter side and 10 mm in height) and a length of 50 mm with a Z axis pitch of 1.0 mm. After subjecting their surface to plasma treatment by the same method of Example 1-(2), the resulting fabric was soaked for 24 hours in 1.0% hyaluronic acid aqueous solution ($\overline{M}w$: 1,800,000) and then subjected to the same crosslinking treatment of Example 4 to obtain a three-dimensional fabric structure whose surface was covered with hyaluronic acid gel. A diepoxy compound (copolymer of ethylene, propylene glycol and diglycidyl ether) was used as the crosslinking agent. By the crosslinking, decomposition of the hydrogel was prevented. In addition, adhesion between the fibers and the gel was improved by the plasma treatment.

Unlike the case of Example 4, these fibers are not biologically degradable and can maintain their strength in the living body for a prolonged period of time. Because of this feature, this structure is useful as a substitute of a biological tissue which requires maintenance of strength for a prolonged period of time. Since this structure is a cubic body of dense fiber fabric, its connection by the yarn is possible, so that its development as a joint cartilage is possible. For example, it is useful as a substitute of menisci due to its surface lubricity by the hyaluronic acid gel. In addition, mixing of the hyaluronic acid gel with unsinderted HA, AW, delimed bone or BMP (bone morphogenetic protein) will result in a base material by which enhancement of the induction and formation of a bone can be expected.

INDUSTRIAL APPLICABILITY

As is evident from the above description, the implant material of the present invention uses as its base material a bulk structure which comprises a three-dimensional woven or knitted fabric of organic fibers or a composite fabric thereof and has biodompatibility [surface and bulk compatibility (mechanical and structural consistency)]. Therefore, the inventive material exerts eminent effects that it is free from a problem of causing interlayer destruction which is found in the prior art composites, that it has high mechanical strength and durability in three-dimensional directions so that it can withstand its implantation for a prolonged period of time, that it can synchronize with the stress from biological tissues by delicately changing its deformation characteristics in each direction by properly selecting woven/knitted fabric, that it has a capacity to be penetrated by biological tissues into its fabric space, that it does not cause foreign body reaction or can be positively connected to its surrounding biological tissues, and that it has capacity to be implanted for a prolonged period of time.

We claim:

1. An implant material which comprises, as a base material, a biocompatible bulk structure of a tri-axial or more three-dimensionally woven fabric of organic fibers, a tri-axial or more three-dimensionally knitted fabric of organic fibers or a combination thereof.

2. The implant material according to claim 1, wherein a void ratio in the fabric of the bulk structure is in the range of from 20 to 90 vol %.

3. The implant material according to claim 1 or 2, wherein the organic fibers which constitute the bulk structure are bioinert fibers or fibers having a surface coated with a bioinert polymer.

4. The implant material according to claim 1, wherein the organic fibers which constitute the bulk structure are bioactive or bioaffinitive fibers.

5. The implant material according to claim 1, wherein the organic fibers which constitute the bulk structure are biologically degradable and absorbable fibers.

6. The implant material according to claim 3, wherein the bulk structure has a surface that is biologically activated.

7. The implant material according to claim 6, wherein the bulk structure has a surface that is biologically activated by grafting it with a monomer or an oligomer having an organic phosphate group.

8. The implant material according to claim 6, wherein the bulk structure has a surface that is biologically activated by coating it with a biologically degradable and absorbable polymer containing a bioactive substance.

9. The implant material according to claim 6, wherein the bulk structure has a surface that is biologically activated by coating it with a polymer containing a bioactive substance and scraping off the surface of said polymer to expose the bioactive substance.

10. The implant material according to claim 8 or 9, wherein said bioactive substance is at least one substance selected from the group consisting of bioglass, ceravital, hydroxyapatite and AW glass ceramics.

11. The implant material according to claim 6, wherein the bulk structure has a surface that is biologically activated by immobilizing a natural biomaterial to the surface thereof.

12. The implant material according to claim 11, wherein said natural biomaterial is at least one substance selected from the group consisting of collagen, gelatin, fibronectin, hyaluronic acid, thrombomodulin, hydroxyapatite, urokinase and heparin.

13. The implant material according to claim 3, wherein the bulk structure has a surface that is biologically inactivated by immobilizing a highly hydrophilic hydrogel to the surface thereof.

14. The implant material according to claim 13, wherein said highly hydrophilic hydrogel is at least one gel selected from the group consisting of gelatin, methylcellulose, hydroxypropylmethylcellulose, alginic acid, agar, carrageenan, proteoglycan, hyaluronic acid, collagen, fibrin, casein, polyvinyl alcohol gels, polyethylene oxide gels and polyhydroxymethacrylic acid base gels.

15. The implant material according to any one of claims 1 to 14, wherein a matrix of the same or different organic fibers is filled in a fabric space of the bulk structure.

16. The implant material according to claim 15, wherein the bulk structure is compression-molded.

* * * * *

UNITED STATES PATENT AND TRADEMARK OFFICE
CERTIFICATE OF CORRECTION

PATENT NO.    : 5,711,960
DATED         : January 27, 1998
INVENTOR(S)   : Yasuo Shikinami It is certified that error appears in the above-indentified patent and that said Letters Patent is hereby corrected as shown below:

Column 22, line 4 (Claim 6, line 1), change "claim 3" to -- claim 1 --.

Column 22, line 30 (Claim 13, line 1), change "claim 3" to -- claim 1 --.

Column 22, line 41 (Claim 15, line 1), change "any one of claims" to -- claim --; and line 42 (Claim 15, line 2), change "1 to 14," to -- 1, --.

Signed and Sealed this

Fourth Day of August, 1998

Attest:

BRUCE LEHMAN

Attesting Officer

Commissioner of Patents and Trademarks